(12) United States Patent
Maisenhölder et al.

(10) Patent No.: US 6,510,263 B1
(45) Date of Patent: Jan. 21, 2003

(54) WAVEGUIDE PLATE AND PROCESS FOR ITS PRODUCTION AND MICROTITRE PLATE

(75) Inventors: Bernd Maisenhölder, Zürich (CH); Johannes Edlinger, Frastanz (AT); Clause Heine, Chur (CH)

(73) Assignee: Unaxis Balzers Aktiengesellschaft (LI)

(*) Notice: Subject to any disclaimer, the term of this patent is extended or adjusted under 35 U.S.C. 154(b) by 0 days.

(21) Appl. No.: 09/497,129

(22) Filed: Feb. 3, 2000

(30) Foreign Application Priority Data

Jan. 27, 2000 (CH) ........................... 2000 160/00

(51) Int. Cl.[7] .............................................. G02B 6/34
(52) U.S. Cl. ........................................................ 385/37
(58) Field of Search ............................ 385/37; 359/34; 264/1.24, 1.27, 1.31, 1.34, 1.38; 216/80, 41, 48; 430/5, 321; 422/82.11

(56) References Cited

U.S. PATENT DOCUMENTS

| | | | |
|---|---|---|---|
| 4,806,454 A | | 2/1989 | Yoshida |
| 5,004,673 A | | 4/1991 | Vlannes |
| 5,082,629 A | * | 1/1992 | Burgess et al. ........... 422/82.11 |
| 5,413,884 A | * | 5/1995 | Koch et al. ..................... 430/5 |
| 5,480,687 A | | 1/1996 | Heming et al. |
| 5,501,925 A | * | 3/1996 | Smith et al. .................... 430/5 |
| 5,759,744 A | | 6/1998 | Brueck |
| 5,786,116 A | * | 7/1998 | Rolfson ......................... 430/5 |
| 5,982,963 A | | 11/1999 | Feng |
| 6,013,396 A | * | 1/2000 | Capodieci ....................... 430/5 |
| 6,218,194 B1 | * | 4/2001 | Lyndin et al. .............. 436/518 |

FOREIGN PATENT DOCUMENTS

| | | |
|---|---|---|
| DE | 4410258 | 10/1994 |
| EP | 0566886 | 10/1993 |

* cited by examiner

Primary Examiner—Rodney Bovernick
Assistant Examiner—Mike Stahl
(74) Attorney, Agent, or Firm—Crowell & Moring LLP

(57) ABSTRACT

A waveguide plate comprising a glass substrate (10) covered with a waveguide layer (2) has coupling grating strips following one another a distance apart, in which the coupling angle changes along parallel lines by not more than 0.1°/cm, preferably not more than 0.05°/cm. The deviation from its mean value over the total waveguide plate is not more than 0.3°, preferably not more than 0.15°. The waveguide plate is suitable as part of a microtiter plate for chemical analyses by means of fluorescence excitation. For its production, the glass substrate (1) is covered with a photoresist layer (10) and exposed to a mercury vapour lamp via a deflecting mirror through a phase mask in the vicinity of which it is arranged, for example at the Littrow angle ($\theta_L$) or at a right angle, then structured by reactive ion etching and provided with the waveguide layer (2) by reactive DC magnetron sputtering, in particular pulsed DC sputtering or AC-superposed DC sputtering.

11 Claims, 5 Drawing Sheets

WAVEGUIDE PLATE AND PROCESS FOR ITS PRODUCTION AND MICROTITRE PLATE

FIELD OF THE INVENTION

The invention relates to a waveguide plate and a process for its production and a microtitre plate comprising such a waveguide plate and as used, for example, for analytical purposes in the biochemical and medical sector.

PRIOR ART

U.S. Pat. No. 5,675,691 discloses a waveguide plate of the generic type, in which coupling gratings are produced by applying a waveguide layer comprising $TiO_2$, $Ta_2O_5$, $HfO_2$, $Y_2O_3$, $Al_2O_3$, $Nb_2O_5$, nitride or oxynitride of Al, Si or Hf to a substrate comprising glass, in particular quartz glass, ceramic or predominantly organic material, it being possible to provide a 20 nm thick intermediate layer, e.g. of $SiO_2$, and to structure said waveguide layer by ablation or modification of the refractive index by means of exposure to two superposed beams of an excimer laser or to a beam modified by a mask. Instead, it is also possible to structure an intermediate layer, e.g. comprising $TiO_2$, in which the ablation barrier is lower and which is applied either to the waveguide layer or directly to the substrate and, in the latter case, is superposed by the waveguide layer after structuring. The grating constants are, for example, 375 nm or 440 nm. The grating area is freely selectable and may be, for example, 1 mm×1 mm or 8 mm×8 mm.

U.S. Pat. No. 5,822,472 discloses a waveguide plate for chemical analyses which bears a 40 nm to 160 nm thick waveguide layer comprising $TiO_2$, ZnO, $Nb_2O_5$, $Ta_2O_5$, $HfO_2$ or $ZrO_2$ on a carrier comprising plastic, glass or quartz. An intermediate layer comprising nonluminous material of low refractive index, e.g. quartz of, for example, 100 nm thickness, where it simultaneously serves as an adhesion promoter, may be arranged in between. An incoupling grating and an outcoupling grating are provided, which are created by known photolithographic or holographic and etching methods in the carrier or in the waveguide layer and have a grating constant of between 200 nm and 1000 nm. The grating may have dimensions of 2 mm (parallel lines)×4 mm with a total area of the waveguide plate of 12 mm×20 mm.

J. Dübendorfer and R. E. Kunz: "Compact integrated optical immunosensor using replicated chirped grating coupler sensor chips", Applied Optics, 37/10 (1.4.1998) discloses a waveguide plate comprising a polycarbonate carrier plate into which a modulated incoupling grating having a grating constant varying between 420 nm and 422.8 nm and an outcoupling grating having a grating constant varying between 595.1 nm and 600.8 nm were impressed. Thereafter, a $TiO_2$ waveguide layer having a thickness of 137 nm and a refractive index of 2.346 was applied by means of low-temperature DC magnetron sputtering, and finally the waveguide plate was silanized. The incoupling angle is −9.5° and the outcoupling angle is 22.5°.

U.S. Pat. No. 5,738,825 describes a microtitre plate on whose underside a 20 nm to 1000 nm, preferably 30 nm to 500 nm, thick waveguide layer comprising $TiO_2$, $Ta_2O_5$, $HfO_2$, $ZrO_2$, $SiO_2$, $Si3N_4$, $Al_2O_3$, $Nb_2O_5$, nitride or oxynitride of Al, Si or Hf is mounted and is covered by a plastics layer. Incoupling and outcoupling gratings are mounted underneath each cavity. The gratings have a grating constant between 330 nm and 1000 nm, in particular about 400 nm to 800 nm, and are produced by lithographic or mechanical methods.

CH-A-688 165 discloses a waveguide plate comprising a substrate of plastic, e.g. polycarbonate, whose surface was structured mechanically, by thermoforming or embossing or during injection moulding, in particular provided with a coupling grating, and carries a waveguide layer applied by a PVD method and comprising $TiO_2$, $Ta_2O_5$, $ZrO_2$, $Al_2O_3$, $SiO_2$—$TiO_2$, $HfO_2$, $Y_2O_3$, $Nb_2O_{51}$, silicon nitride, oxynitride, $SiO_xN_y$, $HfO_xN_y$, $AlO_xN_y$, $TiO_xN_y$, $MgF_2$ or $CaF_2$. To reduce the evaporation losses, an approx. 20 nm thick intermediate layer applied to the substrate before the waveguide layer and comprising an inorganic dielectric material, such as $SiO_2$, is provided and simultaneously serves as an adhesion promoter.

All waveguide plates described above are produced by processes with which no satisfactory uniformity of the coupling grating can be achieved, so that the coupling angle varies relatively widely. Consequently, the relative angle of the exposure unit and of the waveguide plate has to be optimized in a complicated manner in each step during use. Some of the processes described are also very complicated or do not permit very large quantities of constant quality.

EP-A-0 602 829 discloses a process for producing a grating structure on a substrate, for example for a DBR semiconductor laser, in which first a phase mask is produced and then the substrate, e.g. InP, is exposed at the Littrow angle through the phase mask. The exposure can be effected by means of an Hg—Xe arc lamp having a light source diameter of 0.25 mm, three lines around 365 nm wavelength being filtered out. The substrate is located close to the phase mask, i.e. at a distance of not more than 10 μm.

To produce the phase mask, a quartz substrate is covered with three layers, a photoresist layer, a thin germanium layer and finally a layer of a resist sensitive to electron beams. The uppermost layer is then structured by inscribing by means of electron beams, developing the uppermost layer and removing the unexposed parts. The structure is transferred to the layers underneath by reactive ion etching, initially with $CF_3Br$ and then with $O_2$, and finally to the quartz substrate itself by a further step of reactive ion etching, whereupon the residues of the layers are removed. The grating constant may be, for example, between 190 nm and 250 nm. The phase mask may be several centimeters long and the grating may extend over its entire length. However, the length of the lines is as a rule only 5–20 μm. Greater lengths are possible but require very long processing times. In practice, gratings of more than 1 $mm^2$ can scarcely be produced with reasonable effort and good accuracy. In particular, stitching errors during inscribing by means of electron beams cannot be avoided.

SUMMARY OF THE INVENTION

It is the object of the invention to provide a waveguide plate which permits feasible rapid analysis with little effort. In addition, it is intended to provide a microtitre plate based on such a waveguide plate. As a result of the limits which are narrow also with large grating lengths and within which the coupling angle varies, it is possible simultaneously to expose and to read out larger parts of the waveguide plate or microtitre plate. Successive exposures of different parts of the waveguide plate or microtitre plate are also simplified since reoptimization of the relative angle between it and the exposure unit is either not required or in any case is very easy.

Furthermore, it is the object of the invention to provide a process for producing a waveguide plate according to the invention, which permits the creation of large gratings in particular having long parallel lines with great precision, provides freedom of design with regard to the arrangement of the gratings and is simple and economical. The process according to the invention furthermore permits the production of large series of waveguide plates of constant quality and having optical properties, such as coupling efficiencies and in particular coupling angles, which are within narrow limits.

BRIEF DESCRIPTION OF THE DRAWINGS

The invention is explained in more detail below with reference to Figures, which represent only one embodiment.

DESCRIPTION OF THE PREFERRED EMBODIMENTS

Figure 1:
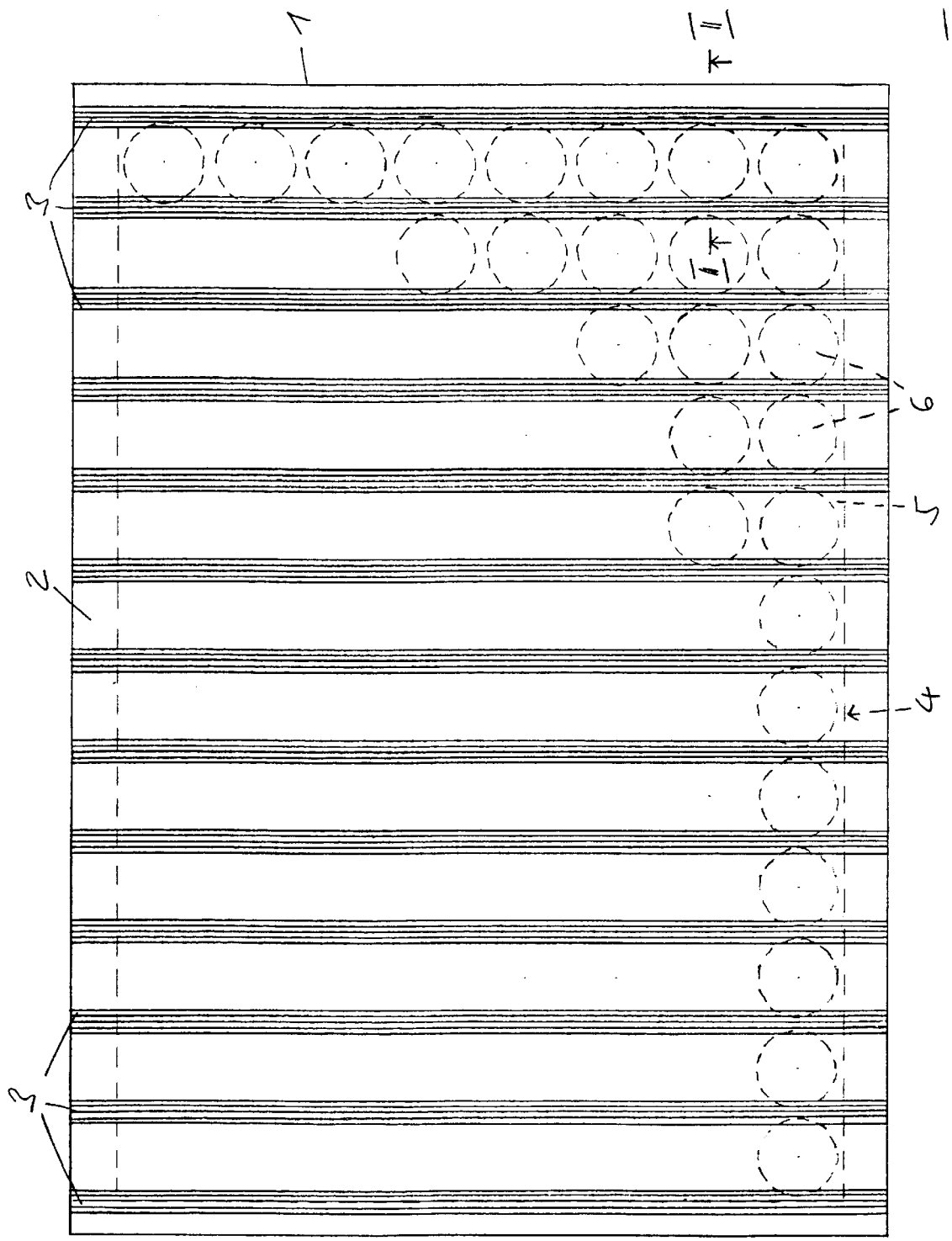
FIG. 1 shows a plan view of a waveguide plate according to the invention, having an attachment which is indicated by a dashed line and supplements it to form a microtitre plate.

The waveguide plate according to the invention consists (FIGS. 1, 2, the diagrams are schematic and not to scale) of glass substrate 1, for example of AF 45 from Schott DESAG, having dimensions of 102 mm×72 mm and a thickness of 0.7 mm, which carries on one side a 150 nm thick waveguide layer 2 comprising $Ta_2O_5$. Its refractive index at a wavelength of 633 nm is 2.11.

A plurality of parallel coupling grating strips 3 which are a distance apart and extend in parallel lines each over the entire width of the waveguide plate are present on the surface carrying the waveguide layer 2. The width of each of the coupling grating strips 3 is 0.5 mm. The grating period is $\Lambda$=360 nm, the groove/land ratio is about 1:1, and the grating depth is about 20 nm. The parameters defining the grating are each maintained very accurately over the total length of the coupling grating strip. Consequently, changes in the coupling angle $\theta$ at which a light beam directed from below through the glass substrate 1 at the coupling grating strip 3, in particular having a wavelength of about 633 nm, is coupled into the waveguide layer 2 with maximum coupling efficiency remains within very narrow limits. Along the lines of a coupling grating strip 3, said angle changes by not more than 0.05°/cm. On the total waveguide plate, the deviation of the coupling angle $\theta$ from the mean value, which in the case described corresponds to 2.31°, remains below 0.15°.

Figure 2:
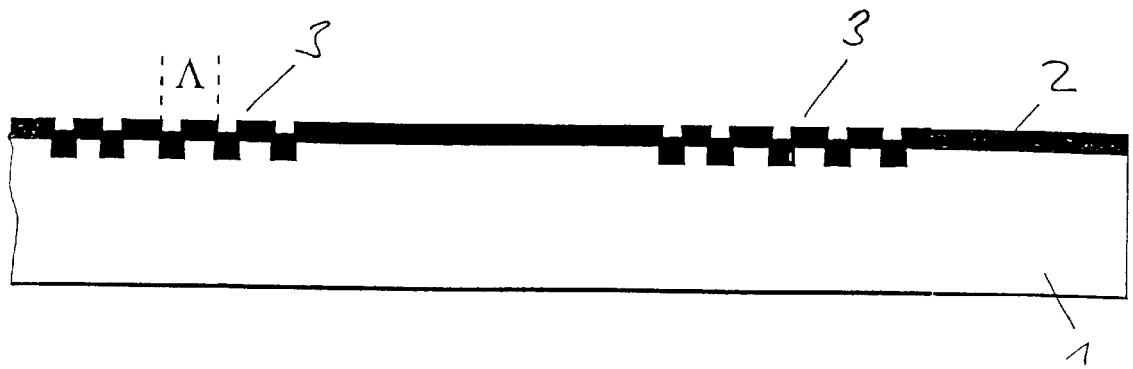
FIG. 2 shows a section along II—II in FIG. 1, FIG. 3 schematically shows the use of a microtitre plate comprising a waveguide plate according to the invention.
Figure 3:
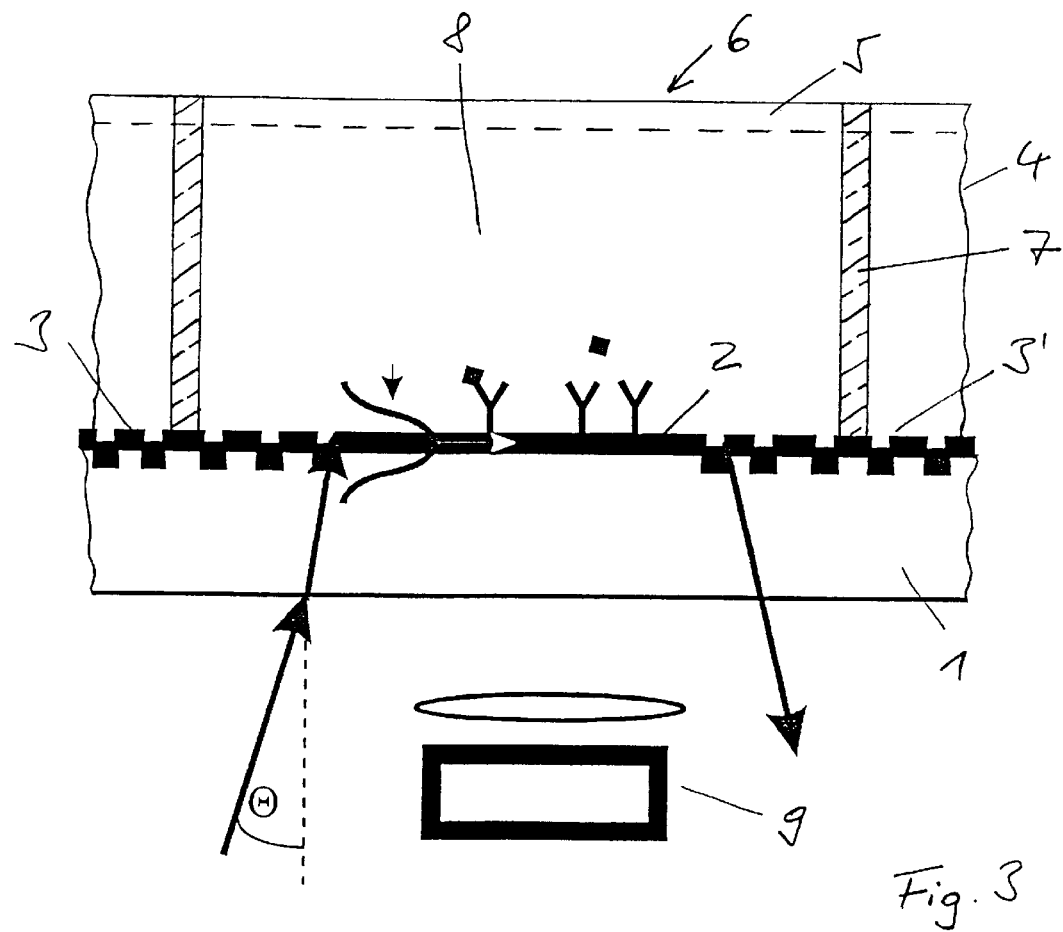

As shown in FIG. 3 and indicated in FIG. 1, the waveguide plate is supplemented by a honeycomb-like attachment 4 of plastic to give a microtitre plate for use for chemical analysis, in particular of biological substances. The attachment has a cover plate 5 which is perforated by round openings 6 arranged in a regular grid and of, for example, about 8 mm diameter. At each of the openings 6, a tube section 7 which is open at the bottom, laterally bounds a cavity 8 and is tightly connected, for example adhesively bonded, at the lower end to the waveguide plate 2 and connects to the underside of the cover plate 5.

If it is intended to investigate the content of a cavity 8 with respect to the concentration of specific molecules, an adjacent coupling grating strip 3 of the waveguide plate 2 is exposed in a manner known per se by means of a suitable light source at the coupling angle $\theta$ to light of a specific wavelength, in the example to light of 633 nm wavelength by means of an He—Ne laser. The light passed through the waveguide layer 2, which forms the base of the cavity 8, to the adjacent coupling grating strip 3' and coupled out there excites molecules in the cavity 8 to produce fluorescence, which is registered by an optical system 9 and then analyzed. The high accuracy with which the coupling angle $\theta$ is maintained over the length of the coupling grating strip 3 permits simultaneous investigation, with high efficiency, of cavities arranged along said coupling grating strip. Since the coupling angle $\theta$ deviates only slightly from the mean value over the total waveguide plate 2, however, no complicated optimization of said angle is required for investigating the next row of cavities 8.

Figure 4A:
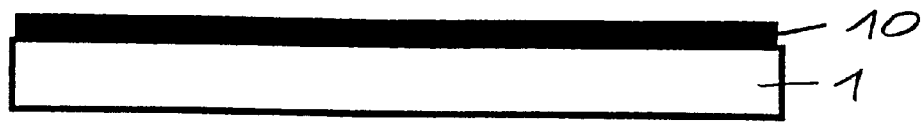
FIGS. 4a–e show different steps in the production of a waveguide plate according to the invention, FIG. 5 schematically shows the setup used for exposing the photoresist layer during the production of the waveguide plate according to the invention.

To produce the waveguide layer 2, first a photoresist, e.g. AZ1518, diluted 1:4 with AZ1500, both with Clariant, is applied at 1300 rpm to the glass substrate 1, as shown schematically in FIG. 4a–e, and then baked for 30 min at 90° C. in an oven, after which Aquatar from the same manufacturer is applied at 1400 rpm and once again baked for 15 min at 90° C. in an oven. The photoresist layer 10 thus produced has a reflectivity of less than 1% (FIG. 4a).

Figure 5:
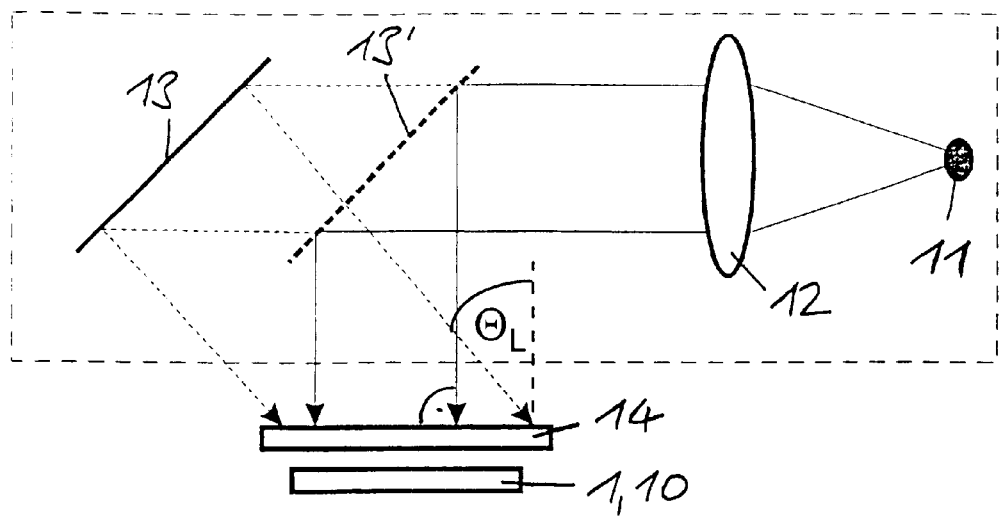

In a subsequent step, the photoresist layer 10 is exposed for 70 sec. For this purpose, the glass substrate 1 is introduced into a setup according to FIG. 5, a mask aligner MA4 from Suss, Munich, which comprises a modified mercury vapour lamp 11 having a modified down-circuit optical system 12 and deflecting mirror 13. The optical system 12 comprises a bandpass filter which, for example, filters out the I-line at a wavelength of 365 nm, and a polarizer, which preferably produces s-polarization. To improve the parallelism of the beams, the fly's eye is removed from the beam path and a lamp with as small an arc as possible is used and is positioned as far away from the substrate as possible.

Figure 7A:
Figure 7B:
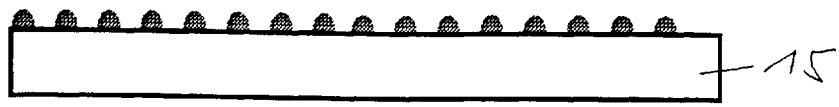
Figure 7C:
Figure 7D:
Figure 7E:
Figure 7F:
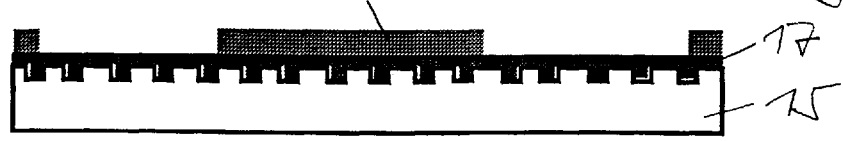
Figure 7G:
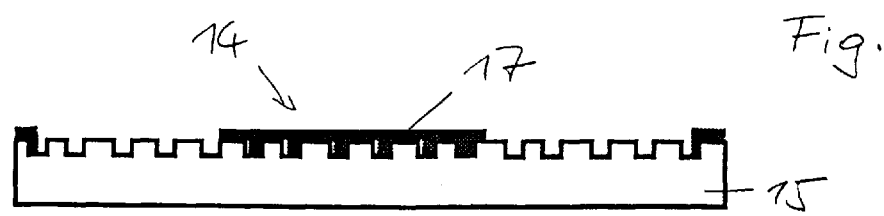

The exposure is performed through a phase mask 14. It comprises a substrate of a transparent material, in the example quartz, with a diffraction grating which carries a structured layer of nontransparent material, in the example chromium, which in this case is interrupted by strips following one another at regular intervals. Phase masks of this type and are manufactured approximately as follows:

A quartz substrate 15 is covered with a photoresist layer 16 (FIG. 7a) and the latter is exposed to light by the two-beam interference method and developed (FIG. 7b). Such structure can be obtained from Ibsen in Farum (Denmark). Thereafter, a diffraction grating is produced on the surface of the quartz substrate 15 by etching and subsequent removal of the photoresist over the whole area (FIG. 7c). Said surface is then completely covered with a chromium layer 17 (FIG. 7d). A continuous photoresist layer 18 is then applied to the chromium layer 17 (FIG. 7e) and exposed through a mask structured by inscribing by means of electron or laser beams. The photoresist is then developed (FIG. 7f) and the chromium layer 17 is removed by etching from the parts not covered by photoresist. Finally, the residues of the photoresist layer 18 are removed to complete the phase mask 14 (FIG. 7g). The structure of the mask thus determines which parts of the phase mask are transparent.

Figure 6:
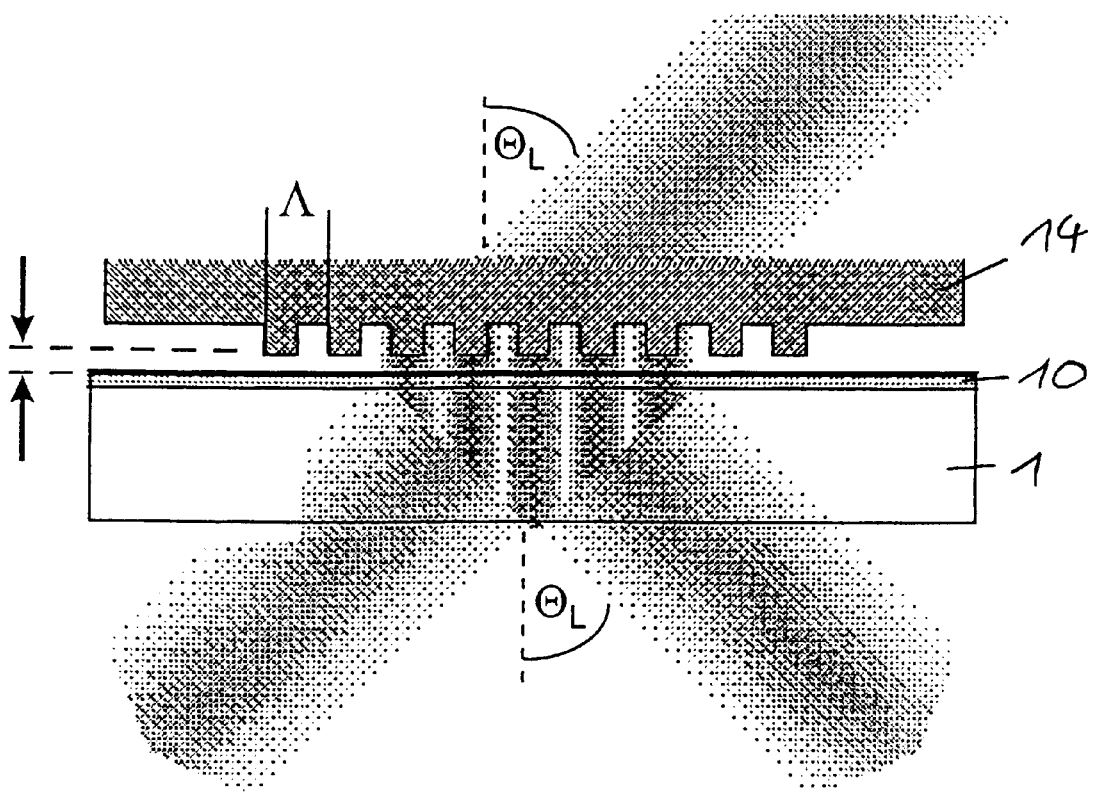
FIG. 6 shows the phase mask and the glass substrate with the photoresist layer under exposure and FIGS. 7a–g show different steps in the production of a phase mask for the production of a waveguide plate according to the invention.

The glass substrate 1 is arranged underneath the phase mask 14 in such a way that the photoresist layer 10 is in vacuum contact with said phase mask. The upper side of the phase mask 14 is exposed at an angle which corresponds approximately to the Littrow angle $\theta_L$ at which the angle of incidence is equal to the angle of first order diffraction, in particular deviates by not more than 10°, preferably not more than 5°, from said angle. Under these conditions, a pronounced diffraction pattern whose structure corresponds to that of the grating of the phase mask 14 forms in the vicinity below the transparent regions of the phase mask 14 (FIG. 6). Alternatively, the phase mask 14 can also be exposed at an angle which approximately corresponds to a right angle, in particular deviates therefrom by not more than 10°, preferably not more than 5° (deflecting mirror 13' shown as a dashed line). In this case, the diffraction pattern in the vicinity of the phase mask 14 has half the period of the grating thereof.

Figure 4B:
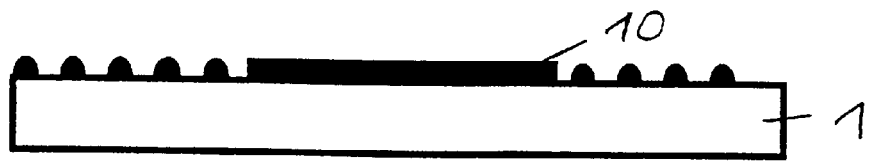
Figure 4C:
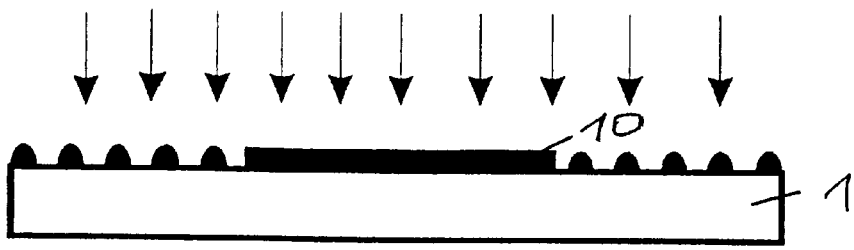
Figure 4D:
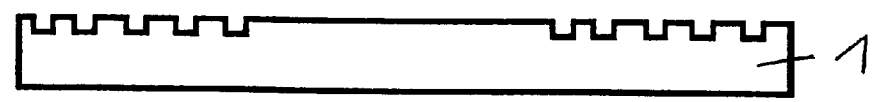

After the exposure, the Aquatar layer is removed by washing with distilled water, and the photoresist is then developed (FIG. 4b). Those parts of the surface of the glass substrate 1 which are not covered with photoresist are then etched with Ar and $CHClF_2$ at a pressure of 0.2 mbar in a parallel-plate reactor with capacitive excitation of the plasma at 13.6 MHz and at an RF power of 50 W. Alternatively, $CHF_3$ could be used for etching. The etch depth is 20 nm. The photoresist is then removed. For this purpose, it is first subjected to reactive ion etching for 60 sec in oxygen plasma at a pressure of 0.2 mbar and at an RF power of 50 W and then detached with Remover AZ100, Deconex and distilled water (FIG. 4d).

Figure 4E:
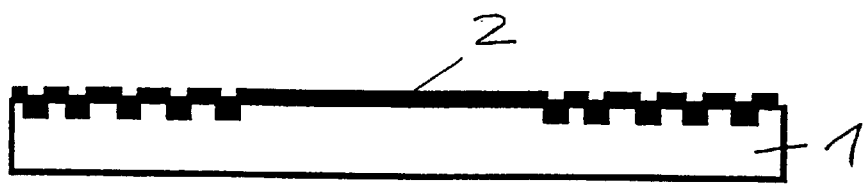

Finally, the waveguide layer 2 is applied by reactive pulsed DC magnetron sputtering or by DC magnetron sputtering superposed with an AC frequency between 1 kHz and 1 MHz, in a Balzers MSP1000 unit, similarly to the procedure described in EP-A-0 508 359 (FIG. 4e). This step is carried out in an $Ar$—$O_2$ atmosphere at a pressure of 3.7 μbar. The target material is tantalum. Finally, the waveguide plate is cut to its final size by wafer sawing.

In particular thanks to the exposure through a phase mask, the process described permits the production of waveguide plates having diffraction coupling gratings in large quantities in a simple manner. The fact that the phase mask is structured by the two-beam interference method also permits the production of large defect-free gratings with high precision, whereas other structuring methods, such as, for example, inscribing by means of electron beams, are not suitable for this purpose owing to the virtually unavoidable stitching errors.

The waveguide plate according to the invention can be modified in many respects without departing from the basic concept of the invention. Thus, it is sufficient for many applications if changes in the coupling angle θ along the grating lines are not more than 0.1°/cm. Furthermore, deviations up to 0.3° or even 0.5° from the mean value over the total waveguide plate are permissible in many cases. It is also possible to produce variable gratings having, for example, a linearly variable line spacing.

Many deviations are possible in the production process too. Thus, for example also in the exposure step decisive for the process, the photoresist layer may be a distance away from the phase mask, which makes it easier to carry out the process. However, it must be arranged in the vicinity, i.e. as a rule at a distance of less than 100 μm, so that the diffraction pattern is sufficiently pronounced. The distance may be approximately between 2 μm and 100 μm. Instead of a mercury vapour lamp, a laser, in particular an excimer laser, may also be used as the light source. In addition to $Ta_2O_5$, other substances are also suitable as materials for the waveguide layer, in particular $Nb_2O_5$, $TiO_2$, $ZrO_2$, $Al_2O_3$, $SiO_2$—$TiO_2$, $HfO_2$, $Y_2O_3$, $SiO_xN_y$, $Si_3N_4$, $HfO_xN_y$, $AlO_xN_y$, $TiO_xN_y$, $MgF_2$ or $CaF_2$.

LIST OF REFERENCE SYMBOLS

1 Glass substrate
2 Wveguide layer
3 Coupling grating strip
4 Attachment
5 Cover Plate
6 Opening
7 Tube section
8 Cavity
9 Optical system
10 Photoresist Layer
11 Mercury Vapour Lamp
12 Optical System
13, 13' Deflecting Mirror
14 Phase Mask
15 Quartz Substrate
16 Photoresist Layer
17 Chromium Layer
18 Photoresist Layer

What is claimed is:

1. A process for producing a waveguide plate having a plate-like glass substrate carrying a waveguide layer with at least one coupling grating, comprising the steps of:

forming a phase mask comprising a transparent region with a diffraction grating and masking parts of said diffraction grating;

covering the glass substrate with a photoresist layer;

arranging the glass substrate in proximity to the phase mask with said photo resist layer facing said phase mask;

exposing said phase mask at an angle which deviates from a Littrow angle ($θ_L$) or from a right angle by not more than 10°;

developing the photoresist layer;

subjecting the glass substrate to an etch process for producing said at least one coupling grating;

removing said photo resist layer; and applying the waveguide layer.

2. The process according to claim 1, wherein the exposure of the photoresist layer is effected by means of a mercury vapour lamp.

3. The process according to claim 1, wherein the phase mask is structured beforehand photolithographically by the two-beam laser interference method.

4. The process according to claim 3, wherein the phase mask is formed by a transparent substrate which carries a layer of a nontransparent material perforated in a structured manner.

5. The process according to claim 4, wherein the substrate is a quartz substrate and the layer of a nontransparent material is a chromium layer.

6. The process according to claim 1, wherein during the exposure of the photoresist layer, the photoresist layer is in vacuum contact with the phase mask.

7. The process according to claim 1, wherein during the exposure of the photoresist layer, the distance between the latter and the phase mask is between 2 μm and 100 μm.

8. The process according to claim 1, wherein the etch process comprises reactive ion etching, with a gas which contains at least one of the following components: Ar, $CHClF_2$, $CHF_3$.

9. The process according to claim 1, wherein the waveguide layer (2) is applied by reactive DC magnetron sputtering, by pulsed DC sputtering or AC-superposed DC sputtering.

10. The process according to claim 1, wherein the phase mask is exposed at an angle which deviates from the Littrow angle ($Θ_L$) or from a right angle by not more then 5°.

11. The process according to claim 1, wherein the coupling grating is formed as a grating of lines with a period between 150 nm and 1000 nm, an extension of said grating being at least 5 cm with lines parallel to one another.

* * * * *